United States Patent [19]

Lenz

[11] Patent Number: 4,618,725

[45] Date of Patent: Oct. 21, 1986

[54] PREPARATION OF α-METHYL-SUBSTITUTED KETONES

[75] Inventor: Hans-Heinrich Lenz, Mannheim, Fed. Rep. of Germany

[73] Assignee: BASF Aktiengesellschaft, Ludwigshafen, Fed. Rep. of Germany

[21] Appl. No.: 744,225

[22] Filed: Jun. 13, 1985

[30] Foreign Application Priority Data

Jun. 15, 1984 [DE] Fed. Rep. of Germany ....... 3422282

[51] Int. Cl.$^4$ ............................................. C07C 45/71
[52] U.S. Cl. .................................... 568/315; 568/347; 568/391; 548/349; 548/579; 544/335; 549/78
[58] Field of Search ...................... 568/347, 391, 315; 548/349, 579; 549/78; 544/335

[56] References Cited

U.S. PATENT DOCUMENTS

| | | | |
|---|---|---|---|
| 2,064,254 | 12/1936 | Fuchs et al. | 568/391 |
| 2,549,520 | 4/1951 | Prichard | 568/347 |
| 2,697,730 | 12/1954 | Mecorney et al. | 568/391 |
| 3,361,828 | 1/1968 | Robbins et al. | 568/391 |
| 3,657,351 | 4/1972 | Araki et al. | 568/391 |
| 3,685,768 | 4/1972 | Pommer et al. | 568/391 |
| 3,781,307 | 12/1973 | Chabardes et al. | 568/391 |
| 3,932,518 | 1/1976 | Arpe | 568/391 |

FOREIGN PATENT DOCUMENTS 2148610  4/1973  Fed. Rep. of Germany ...... 568/391

*Primary Examiner*—James H. Reamer
*Attorney, Agent, or Firm*—Keil & Weinkauf

[57] ABSTRACT

α-Methyl-substituted ketones are prepared by reacting the corresponding unsubstituted ketones, which must possess two or more geminal hydrogen atoms in the α-position, with methanol in the gas phase at from 350° to 500° C. and under from 1 to 20 bar in the presence of a metal oxide.

6 Claims, No Drawings

PREPARATION OF α-METHYL-SUBSTITUTED KETONES

The present invention relates to a novel process for the preparation of α-methyl-substituted ketones by reacting the corresponding unsubstituted ketones with methanol in the gas phase in the presence of a metal oxide.

It is known that higher ketones can be synthesized from the corresponding lower homologs. In the case of chain extension by one carbon atom (methylation), the ketone used as the starting material can be subjected to an aldol reaction with formaldehyde, water eliminated from the adduct formed, and the resulting α,β-unsaturated ketone subjected to a hydrogenation reaction at the C—C double bond.

In another possible procedure, for example, the particular ketone to be reacted is converted to its enolate, which is methylated with a methylating reagent such as methyl halide or dimethyl sulfate (cf. Houben-Weyl Methoden der organischen Chemie, 4th edition, Volume 7/2b, page 1385 et seq.).

The disadvantages of the stated processes are the use of bases, some of which furthermore are very expensive, and the use of highly toxic substances (eg. dimethyl sulfate). Moreover, the vast majority of these processes are multi-stage processes in which the desired products are often formed only in poor yields and with poor selectivity.

J. Chem. Soc. Chem. Commun. 1984, 39, discloses the reaction of acetone with methanol in the gas phase over a supported iron catalyst whose carrier consists of magnesium oxide. In this process, methanol acts as a vinylating agent, ie. the principal product of the reactions described therein is methyl vinyl ketone. The by-products formed include methyl ethyl ketone and undefined saturated and unsaturated ketones of 5 carbon atoms, as well as fairly large amounts of isopropanol, which has presumably been formed as a result of the transfer of hydrogen from methanol to acetone.

According to the above publication, other ketones which possess hydrogen atoms in the α-position would also be expected to react with methanol to give the corresponding vinyl ketones.

In contrast, we have found that, surprisingly, methanol does not act as a vinylating agent, and -methyl-substituted ketones of the general formula

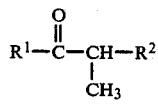

where $R^1$ is unsubstituted or substituted aryl or hetaryl or a tert.-alkyl radical, and $R^2$ is hydrogen or straight-chain or branched alkyl of 1 to 12 carbon atoms, or $R^1$ and $R^2$ together form an unsubstituted or substituted alkylene group —$(CH_2)_n$—, where n is an integer from 3 to 13, are advantageously obtained, if the corresponding unsubstituted ketone, which must possess two or more geminal hydrogen atoms in the α-position, is reacted with methanol in the gas phase at from 350° to 500° C. and under from 1 to 20 bar in the presence of a metal oxide selected from the group consisting of the oxides of the metals cerium, chromium, iron, magnesium and manganese.

The reaction products are α-methyl-substituted ketones of the above general formula in which $R^1$ is an unsubstituted or substituted aryl or hetaryl radical or tert.-alkyl, and $R^2$ is hydrogen or straight-chain or branched alkyl of 1 to 12 carbon atoms, or $R^1$ and $R^2$ together form an unsubstituted or substituted alkylene group —$(CH_2)_n$—, where n is an integer from 3 to 13.

Examples of aryl radicals are phenyl and naphthyl, an examples of hetaryl radicals are pyridyl, pyrimidyl, pyrrolyl, furyl and thienyl. These radicals may be substituted or unsubstituted, suitable substituents being lower alkyl radicals, such as methyl, ethyl, isopropyl or butyl.

Examples of tert.-alkyl radicals are tert.-butyl, tert.-pentyl and 1,1-dimethylbutyl.

$R^1$ is preferably a phenyl or pyridyl radical which is unsubstituted or substituted by a lower alkyl group, or is preferably tert.-alkyl.

$R^2$ is, for example, hydrogen, methyl, ethyl, propyl, isopropyl, butyl, sec.-butyl or tert.-butyl.

Where $R^1$ and $R^2$ together form an alkylene radical —$(CH_2)_n$—, n is a integer from 3 to 13, preferably 3, 5, 6 or 10. The alkylene radical may be unsubstituted or monosubstituted, disubstituted or polysubstituted, suitable substituents being lower alkyl radicals, eg. $C_1$-$C_6$-alkyl, such as methyl, ethyl, isopropyl or butyl.

A special type of substitution of the alkylene radical consists in bridging, for example with formation of a bicyclic system.

Particular examples of alkylene radicals —$(CH_2)_n$— are propylene, pentylene, hexylene and decylene.

The starting materials used are the corresponding unsubstituted ketones, which must possess two or more geminal (ie. bonded to the same carbon atom) hydrogen atoms in the α-position.

Where two geminal hydrogen atoms are present in the α-position, a methyl group is incorporated at this position in the process according to the invention (in the formula, $R^2$ is alkyl). Further methylation is not observed.

Where the ketones used as starting materials possess three geminal hydrogen atoms in the α-position (methyl ketones), it is possible for either one methyl group ($R^2$ is H in the formula) or two methyl groups ($R_2$ is methyl in the formula) to be selectively incorporated at this position.

Usually, the monomethyl product is first selectively obtained in this case. By a suitable choice of reaction conditions, for example a longer residence time in the reactor or a higher reaction temperature, it is also possible to obtain the dimethyl product directly.

In the case of cyclic starting ketones, the methylation can take place in the α- and α,α'-positions.

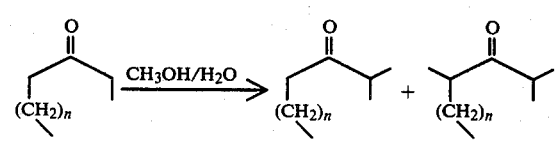

Cyclopentanone, cycloheptanone, cyclooctanone and cyclododecanone can be methylated or bismethylated, with good selectivities, in the α- and α,α'-positions, respectively. The ratio of the two products can be varied by changing the temperature and residence time. By recycling the monomethyl derivative, the selectivity can be shifted completely to the α,α'-dimethylcycloalkanone. A high selectivity with respect to the monomethyl derivative can be achieved by low conversion of the starting material (see below). The most important by-products are α,β-unsaturated ketones and cycloalkanols presumably formed as a result of hydrogen transfer from the methanol to the ketone. This also explains the low selectivity when cyclohexanone is used; aromatization results in phenol, o-cresol and 2,6-dimethylphenol. α- and β-tetralone likewise tend to undergo aromatization. In contrast, geminally disubstituted cyclohexanone can be methylated in good yields:

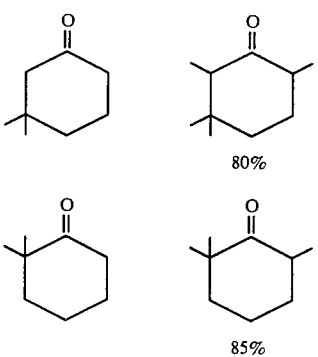

When the ketones containing a six-membered ring are not geminally disubstituted, there is a tendency to aromatization.

If a bicyclic starting ketone is methylated, a mixture of endo- and exo-α-methylcamphor in a molar ratio of 3:1 is obtained, as shown in the equation below:

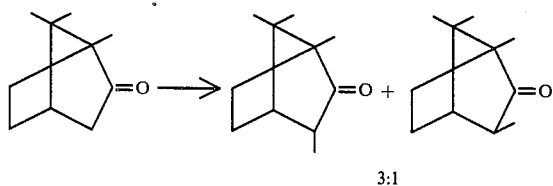

3:1

The cycloalkanols are preferably reacted with an excess of methanol in the presence of water at 400°–480° C., in particular 400°–450° C., preferably over a magnesium oxide catalyst.

The process according to the invention is carried out in the presence of a catalyst, ie. a metal oxide selected from the group consisting of the oxides of the metals cerium, chromium, iron, magnesium and manganese. Examples are cerium(IV) oxide, chromium(III) oxide, iron(III) oxide, magnesium oxide and manganese(II) oxide, magnesium oxide being preferably used.

The preparation of these metal oxides is known, the products being commercially available. As is usual in catalyst technology, they are advantageously employed in the molded state, for example in the form of tablets, extrudates, pills, spheres or rings.

The novel process is carried out in the gas phase at from 350° to 500° C., preferably from 400° to 450° C., and under from 1 to 20 bar, preferably under atmospheric pressure.

The molar ratio of the two reactants, ie. the ketone and methanol, is from 1:1 to 1:10, preferably from 1:2 to 1:4.

In some cases, it is advantageous to effect the reaction in the presence of water, the latter preferably being added in an amount such that the molar ratio of water to ketone is from 1:1 to 5:1.

The novel process is advantageously carried out as follows: a mixture of the reactants in the stated molar ratio, in the presence or absence of water, is first fed continuously to an evaporator, where complete vaporization is effected. In this procedure, the resulting gas mixture is brought to a temperature which is similar to the reaction temperature required in the reactor. Advantageously, however, a somewhat higher temperature is chosen in the evaporator in order to compensate for any heat losses which may occur on the way to the reactor.

The gas mixture then enters the reactor, which has been heated to the required reaction temperature. A tube reactor which contains the catalyst is advantageously used as the reactor.

The space velocity chosen is typically, for example, from 250 to 450 ml (based on the state of liquid aggregation) of liquid reaction mixture per liter of catalyst per hour , but is not restricted to this range.

The residence time in the reactor is about 6–5 sec. In the case of double methylation (see above), it is advisable to to maintain a residence time of about 6–20 sec.

The gaseous reaction mixture leaving the reactor is then condensed, after which it can be purified by fractional distillation.

The advantage of the novel process is the controlled course of the reaction, ie. by-products, such as the toxic vinyl ketones and their polymers or the alcohols formed by hydrog n transfer from methanol to the ketone, are produced in only small amounts.

Moreover, the excess amount of methanol used is substantially smaller than that usually employed in the prior art.

Finally, the conversion of the ketone used is very high (from 65 to 100%), while at the same time the desired products are formed with high selectivity. This is surprising since the known process (loc. cit.) gives only poor selectivities at low conversion (not more than 37.2%), and the selectivities usually decrease further as the conversion increases.

The methylated ketones obtained by the novel process are useful intermediates for the synthesis of crop protection agents. Some of them are also important as scents.

The examples which follow illustrate the invention.

EXAMPLE 1

120 ml/hour (corresponding to 92.5 g/hour) of a mixture of 100 g of 2,2-dimethylbutan-3-one, 128 g of methanol and 18 g of water were vaporized continuously, and the vapor passed over 400 ml of magnesium oxide in tablet form. The resulting gaseous reaction product was condensed, and analyzed by gas chromatography. When methanol and water had been stripped off, the following results were obtained (in % by weight):

|  | Reaction temperature | |
|---|---|---|
|  | 410° C. | 425° C. |
| 2,2-dimethylpentan-3-one | 61.5 | 62.0 |
| 2,2,4-trimethylpentan-3-one | 3.9 | 4.1 |
| 2,2-dimethylbutan-3-one | 24.8 | 20.9 |

EXAMPLE 2

120 ml/hour (corresponding to 103 g/hour) of a mixture of 134 g of propiophenone, 128 g of methanol and 18 g of water were vaporized continuously, and the vapor passed over 400 ml of magnesium oxide in tablet form. The resulting gaseous reaction mixture was condensed, and analyzed by gas chromatography. When methanol and water had been stripped off, the following results were obtained (in % by weight):

|  | Reaction temperature | |
|---|---|---|
|  | 420° C. | 460° C. |
| 1-phenyl-2-methylpropan-1-one | 46.6 | 64.7 |
| propiophenone | 34.1 | 15.8 |

EXAMPLE 3

120 ml/hour (corresponding to 101 g/hour) of a mixture of 121 g of 3-acetylpyridine, 320 g of methanol and 36 g of water were vaporized continuously, and the vapor passed over 400 ml of magnesium oxide in tablet form. The resulting gaseous reaction mixture was condensed, and analyzed by gas chromatography. When methanol and water had been stripped off, the following results were obtained (in % by weight):

|  | Reaction temperature | |
|---|---|---|
|  | 400° C. | 420° C. |
| 1-pyrid-3-ylpropan-1-one | — | — |
| 1-pyrid-3-yl-2-methylpropan-1-one | 67.2 | 48.0 |
| 1-pyrid-3-yl-2-methylpropan-1-ol | 19.3 | 26.5 |
| 3-acetylpyridine | — | — |

EXAMPLES 4 TO 8

In Examples 4 to 8, cyclic ketones were employed. The particular cycloalkanone, together with an excess of methanol and in the presence of water, was passed over the MgO catalyst with various residence times. The temperature was from 400° to 450° C. Conversions and selectivities are summarized in the Table below.

TABLE 1

| Ring size (n + 2) | α-alkylation of cycloalkanones | | | |
|---|---|---|---|---|
|  | Conversion [%] | Selectivity [%] | | |
|  |  | Monomethyl | Dimethyl | Σ |
| 5 | 82 | 40 | 36 | 76 |
| 6 | 93 | 21 | 25 | 46 |
| 7 | 88 | 24 | 48 | 72 |
| 8 | 80 | 46 | 30 | 76 |
| 12 | 94 | 46 | 33 | 79 |

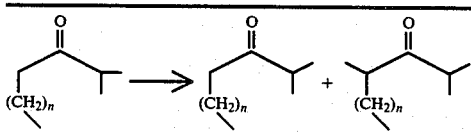

EXAMPLE 9

2-Methylcyclopentanone is an intermediate for an aroma. In the methylation of the cyclopentanone, the reaction temperature, the residence time and the molar ratio of the reactants were varied in order to investigate the effect of these parameters on conversion and selectivity. The results are summarized in Table 2 below.

TABLE 2

Variation of the process parameters in the preparation of 2-methylcyclopentanone

| Temperature [°C.] | Residence time [sec] | Molar ratio CH₃OH:cyclopentanone | Conversion [%] | Selectivities [%] | |
|---|---|---|---|---|---|
|  |  |  |  | α-Methyl | α,α'-Dimethyl |
| 400 | 4 | 15:1 | 70 | 20 | 15 |
| 400 | 2 | 15:1 | 55 | 25 | 11 |
| 420 | 2 | 15:1 | 75 | 16 | 19 |
| 400 | 5 | 5:1 | 54 | 32 | 9 |
| 420 | 5 | 5:1 | 69 | 24 | 12 |
| 420 | 6 | 2:1 | 41 | 47 | 8 |
| 420 | 7 | 1:1 | 27 | 60 | 4 |
| 440 | 7 | 1:1 | 36 | 61 | 6 |
| 460 | 7 | 1:1 | 46 | 59 | 6 |

I claim:

1. A process for producing α-methyl-substituted ketones of the formula

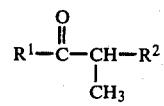

wherein $R^1$ is unsubstituted or substituted aryl or hetaryl or a tert.-alkyl radical, and $R^2$ is hydrogen or straight-chain or branched alkyl of 1 to 12 carbon atoms, or $R^1$ and $R^2$ together form an unsubstituted or substituted alkylene group —$(CH_2)_n$—, where n is an integer from 3 to 13, wherein the corresponding unsubstituted ketone, which must possess two or more geminal hydrogen atoms in the α-position, is reacted with methanol in the gas phase at from 350° to 500° C. and under from 1 to 20 bar in the presence of a magnesium oxide catalyst.

2. A continuous process for producing α-methyl-substituted ketones of the formula

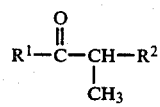

wherein $R^1$ is unsubstituted or substituted aryl or hetaryl or a tert.-alkyl radical, and $R^2$ is hydrogen or straight-chain or branched alkyl of 1 to 12 carbon atoms, or $R^1$ and $R^2$ together form an unsubstituted or substituted alkylene group —$(CH_2)_n$—, where n is an integer from 3 to 13, wherein the corresponding unsubstituted ketone, which must possess two or more geminal hydrogen atoms in the α-position, is reacted with methanol in the gas phase at from 350° to 500° C. and under from 1 to 20 bar in the presence of a magnesium oxide catalyst, and wherein the reaction is carried out using a molar ratio of ketone to methanol of from 1:1 to 1:10.

3. The process of claim 1, wherein $R^1$ is unsubstituted or lower alkyl substituted phenyl, naphthyl, pyridyl, pyrimidyl, pyrrolyl, furyl or thienyl, or is tert.butyl, tert.pentyl or 1,1-dimethyl-butyl.

4. The process of claim 2, wherein $R^1$ is unsubstituted or lower alkyl substituted phenyl, naphthyl, pyridyl, pyrimidyl, pyrrolyl, furyl or thienyl, or is tert.butyl, tert.pentyl or 1,1-dimethyl-butyl.

5. The process of claim 1, wherein the reaction is carried out from 400° to 450° C.

6. The process of claim 2, wherein the reaction is carried out from 400° to 450° C.

* * * * *